United States Patent [19]

Yarmush et al.

[11] Patent Number: 5,003,047

[45] Date of Patent: Mar. 26, 1991

[54] METHOD FOR PURIFYING BIOLOGICALLY ACTIVE LIGATE

[75] Inventors: Martin L. Yarmush, Sharon; William C. Olson, Brookline, both of Mass.

[73] Assignee: Massachusetts Institute of Technology, Cambridge, Mass.

[21] Appl. No.: 295,442

[22] Filed: Jan. 10, 1989

[51] Int. Cl.$^5$ .......................... C07K 3/18; C07K 3/20
[52] U.S. Cl. .................................. 530/413; 530/412; 530/421; 530/427
[58] Field of Search ................ 530/412, 413, 427, 421

[56] References Cited

FOREIGN PATENT DOCUMENTS

86/00910 2/1986 World Int. Prop. O. .

OTHER PUBLICATIONS

Morild, E., 1981, Advances in Protein Chemistry, vol. 34:93-166.
Siebenaller, J. F., 1983, Mar. Biol. Lett., 4(4): 233-244 (abstract).
Schade et al., "Kinetics of Reconstitution of Porcine Muscle Lactic Dehydrogenase after Reversible High Pressure Dissociation," Biophysical Chemistry, 11, pp. 257-263, 1980.
Schade et al., "Reversible High-Pressure Dissociation of Lactic Dehydrogenase from Pig Muscle," Biochemistry, vol. 19, p. 1121, 1980.
Hawley, "High-Pressure Techniques," Methods in Enzymology, vol. 19, p. 14.
Harrington et al., "Pressure Effects in Ultracentrifugation of Interacting Systems," Methods in Enzymology, vol. 27, p. 306.
Heremans, "High Pressure Effects on Proteins and Other Biomolecules," Annual Review of Biophysics and Bioengineer, vol. 11, p. 1, 1982.
Heremans et al., "The Interaction of Dyes with Proteins and Nucleic Acids Chemical Relaxation Spectrometry Under High Pressure," Proceedings of the Fourth International Conference on High Pressure, The Physico-Chemical Society of Japan, 1974.
Hawley et al., "An Electrophoretic Study of Reversible Protein Denaturation: Chymotrypsinogen at High Pressures," Biochemistry, vol. 14, No. 14, 1975, p. 3257.
Brandts et al., "Theymodynamics of Protein Denaturation. Effect of Pressure on the Denaturation of Ribonuclease A," Biochemistry, vol. 9, 1970, p. 1038.
Hawley, "Reversible Pressure-Temperature Denaturation of Chymotrypsinogen," Biochemistry, vol. 10, 1971, p. 2436.
Rodgers et al., "Probing the Mechanisms of Macromolecular Recognition: The Cytochrome $b_5$-Cytochrome c Complex," Science, vol. 240, p. 1657, 1988.
Thompson et al., "Effect of Pressure on the Self-Association of Melittin," Biochemistry, vol. 23, No. 15, 1984, p. 3411.
Muller et al., "Thermodynamics and Mechanism of High-Pressure Deactivation and Dissociation of Porcine Lactin Dehydrogenase", Biophysical Chemistry 16, 1982, pp. 1-7.
Muller et al., "Denaturation and Renaturation of Bovine Liver Glutamic Dehydrogenase after Dissociation in Various Denaturants," Z. Naturforsch, 35:2322 (1980).
King et al., "Conformational Drift of Dissociated Lactate Dehydrogenases," Biochemistry, 1986, 25, 3632-3637.
Chryssolmallis et al., "Effect of Hydrostatic Pressure on Lysozyme and Chymotrypsinogen Detected by Fluorescence Polarization," Biochemistry, 1981, 20, 3955-3959.
Kornblatt et al., "Conformations of Cytochrome Oxidase: Thermodynamic Evaluation of the Interconversion of the 418- and 428-nm Forms," Biochemistry, 1982, 21, 5439-4555.
Kornblatt et al., "The Effects of Pressure on Yeast Cytochrome c Peroxidase," Eur. J. Biochm., 159, 39-43 (1986).
Li et al., "Plurality of Pressure-Denatured Forms in Chymotrypsinogen and Lysozyme," Biochemistry, vol. 15, No. 25, 1976, 5571.

Primary Examiner—Margaret Moskowitz
Assistant Examiner—Keith C. Furman
Attorney, Agent, or Firm—Fish & Richardson

[57] ABSTRACT

A method for purifying a biologically active ligate. In this method, a ligand bonded to a first phase and having a specific affinity for the ligate is provided. The ligate is provided with a second phase. The first and second phases are then contacted together under conditions in which the ligand and ligate form a complex bonded to the first phase, with the ligand and ligate held together only by one or more non-covalent pressure sensitive bonds. At least a part of the second phase is then separated from the first phase to provide a purified first phase, and the purified first phase subjected to a pressure of at least 300 atmospheres under conditions sufficient to cause release of the ligate from the complex, but not sufficient to cause significant release of the ligand from the first phase. These conditions do not irreversibly cause biological activity of the ligate to be significantly reduced. The ligate released from the complex is then separated from the immediate vicinity of the ligand, and recovered in its biologically active form.

12 Claims, No Drawings

METHOD FOR PURIFYING BIOLOGICALLY ACTIVE LIGATE

BACKGROUND OF THE INVENTION

The invention was supported in part by grant number CDR-88-03014 from the National Science Foundation. The U.S. government has rights in the invention.

This invention relates to processes for purifying a biologically active ligate. An example of such a process includes affinity chromotography.

Affinity chromatography is a procedure commonly used for purifying a biologically active ligate, for example, a protein, such as an antibody or antigen, or a nucleic acid. Generally, in this procedure a ligand capable of specifically binding to the ligate is bound to a solid phase, such as a glass bead or nitrocellulose membrane. The ligand is bound in a manner which allows the specific binding of the ligate to the ligand. The ligate is then contacted with the bound ligand under conditions in which a ligand/ligate complex is formed on the solid phase, and the solid phase is washed to remove contaminating substances. During washing the complex remains bound to the solid phase. Subsequently, the ligate is caused to separate from the ligand, and thus the solid phase, by provision of an eluting solution. The ligate is then recovered from the eluting solution.

This procedure exploits the specificity of biological interaction between a ligand and a ligate, and is a highly specific method for isolating a biological material. Only a ligate having a sufficient affinity for the ligand on the solid support is retained on that solid support. Other compounds within the sample containing the ligate are not bound to the ligand, and are washed from the solid support during the procedure.

A suitable eluting solution is chosen from a variety of buffers, including solutions containing high concentrations of an acid, a base, a chaotropic salt, or a denaturing agent. This solution causes the ligand/ligate complex to become unstable, and thus release of the ligate into the eluting solution.

SUMMARY OF THE INVENTION

This invention features a method for purifying a biologically active ligate. In this method, a ligand bonded to a first phase and having a specific affinity for the ligate is provided. The ligate is provided within a second phase. The first and second phases are then contacted together under conditions in which the ligand and ligate form a complex bonded to the first phase, with the ligand and ligate held together only by one or more non-covalent pressure sensitive bonds. At least a part of the second phase is then separated from the first phase to provide a purified first phase, and the purified first phase subjected to a pressure of at least 300 atmospheres under conditions sufficient to cause release of the ligate from the complex, but not sufficient to cause significant release of the ligand from the first phase. These conditions do not irreversibly cause biological activity of the ligate to be significantly reduced. The ligate released from the complex is then separated from the immediate vicinity of the ligand, and recovered in its biologically active form.

By ligand and ligate is meant two or more chemical entities which interact to form a complex stabilized by non-covalent bonding, such as hydrogen bonds, hydrophobic interactions and electrostatic forces. Examples of such chemical entities include an antibody, an antigen, a lectin, an enzyme, an enzyme inhibitor, a hormone, a receptor protein, a cytokine, a lipoprotein, a polysaccharide, a nucleic acid, a ribosome, a cell, an enzyme substrate or an analog thereof, a co-enzyme, a monosaccharide, a growth factor, *Staphylococcus aureus* protein A, streptococcal protein G, a nucleic acid binding protein, a nucleotide, a nucleoside, and a group specific dye.

By biologically active is meant that the ligate is recognized by a ligand and the two form a ligand/ligate complex, and that the ligate has an activity commonly associated with that ligate, for example, an enzyme has enzymatic activity, and a hormone has hormonal activity.

The specific affinity of a ligand for a ligate can be broad or narrow dependent upon the components of the second phase from which the ligate must be purified. Generally, it is desirable that the ligand be able to form a complex only with the specific ligate to be purified, and not with any other component of the second phase. However, if two or more components in the second phase are able to bond to the ligand to form a complex, the ligand has a sufficient specificity for use in this invention if it has a high affinity for the ligate to be purified, and only a low affinity for the other components. Preferably, a significant proportion (e.g., at least 75%) of the complexes formed with the ligand are the desired ligand/ligate complex. For example, a ligand suitable in this invention includes a co-factor able to complex with several enzymes, when it is desired to purify one of these enzymes from a solution which contains none of the other enzymes with which the co-factor can form a complex.

The term "purifying" indicates that a ligate is separated from one or more components of the second phase in which it is provided, but preferably is separated from the majority of contaminating compounds in the second phase, to provide a ligate of greater than 95%, or more preferably 99% purity.

In this invention the pressure selected to cause release of the ligate from the ligate/ligand complex is chosen to be insufficient to cause significant release of the ligand from the first phase. That is, less than about 10% of the bound ligand will be released from the first phase under these pressure conditions. In addition, these conditions are selected to ensure that the biological activity of the ligate is not irreversibly reduced. That is, even if the pressure does cause a loss in the biological activity of the ligate, this activity is regained after the pressure is released and the ligate is recovered. For example, an oligomeric protein may be caused to dissociate under high pressure into a monomeric or lower multimeric form, and thereby lose its biological activity. By placing such a monomer or multimer within a suitable buffer, upon release of the high pressure, it can be caused to reassociate and regain its biological activity. By use of such a procedure an oligomer will generally regain at least 75% of its original biological activity, which is thus not significantly reduced by the method of this invention.

By "immediate vicinity" is meant that the ligate is sufficiently removed from the vicinity of the ligand to prevent a ligate/ligand complex being formed prior to recovering the ligate. The amount of removal required may be minimal, but generally it is better to completely separate the released ligate from the ligand.

In preferred embodiments, the purified first phase is subjected to a pressure under conditions insufficient to cause significant reduction in the biological activity of the ligand; the first phase is chosen from a solid support, a liquid immiscible with the second phase, or a polymer which is readily separable from the second phase, and the ligand is covalently bonded or adsorbed to the first phase; the second phase is a liquid; when the first phase is a solid support, the second phase is separated from that support by washing; when the first phase is a liquid immiscible with the second phase, the first and second phases are separated by decanting one liquid from the other; and when the first phase is a polymer, the first and second phases are separated by heating the purified first phase to a temperature sufficient to cause precipitation of the polymer from the second phase.

In other preferred embodiments, the purified first phase is subjected to a pressure of at least 500 atmospheres, preferably between 500 and 3000 atmospheres, and more preferably between 1000 and 3000 atmospheres, with a maximum of 6000 atmospheres; the steps of subjecting the purified first phase to pressure and separating the released ligate are repeated at least once; substantially all of the second phase is separated from the first phase prior to subjecting the purified first phase to pressure; the ligate released from the ligate/ligand complex is separated from the ligand while pressure is maintained; the ligate released from the ligand/ligate complex is washed from the ligand with a solvent; the ligate released from the complex is subjected to an electric field to remove the ligate from the ligand; and the first phase is precipitated away from the released ligate.

The method of this invention allows separation, and therefore purification, of almost any ligate from a ligate/ligand complex without affecting the biological activity of either the ligate or the ligand. This allows repeated use of a ligand bound to a first phase in the method, since the ligand does not lose its ability to bind and then release the ligate. The cost of ligate purification can thus be reduced, especially where the main expense of purification is in provision of bound biologically active ligand.

The ligate purified by the method of this invention is provided in a biologically active form, in contrast to many prior methods in which the ligate may be denatured, or significantly irreversibly inactivated by an eluting liquid used to release ligate from the ligand/ligate complex.

Other features and advantages of the invention will be apparent from the following description of the preferred embodiments thereof, and from the claims.

DESCRIPTION OF THE PREFERRED EMBODIMENTS

Ligates and ligands useful in this invention are broadly described above. Generally, such ligates and ligands are, or contain on their surfaces, biospecific binding molecules in that they are molecules found in living systems, have a biological activity, and specifically recognize each other. Common examples of such molecules include antigens and antibodies, where an antibody is a highly specific molecule recognizing only one antigen, and an antigen is less specific, generally being recognized by a number of different antibodies. Another example is a strand of nucleic acid, for example, DNA, where the strand of DNA is useful as a specific probe for a particular genetic element of an organism or cell, and for purifying a homologous nucleic acid. Different nucleic acid molecules vary in their binding specificity dependent upon the sequence of nucleotides along their length.

In any particular ligate purification, it is important to determine the ligand best suited for purification of the desired ligate. The ligand is selected to specifically bind to the desired ligate, and not significantly bind to other components which contaminate the solution from which the ligate is purified. An important requirement is that the ligand and ligate have a high affinity for each other so that the ligate/ligand complex is sufficiently stable to allow washing of contaminating components from the ligate/ligand complex. This complex should not be so stable that pressure of greater than 300 atmospheres is unable to release the ligate from the complex. That is, covalent bonds should not be formed between the ligate and the ligand, but rather, non-covalent bonds sensitive to high pressure should be formed. Non-covalent bonds include hydrogen bonds, hydrophobic forces and electrostatic forces. Selection of an appropriate ligand for a chosen ligate is well known in the art, and standard techniques can be utilized to determine the most appropriate ligand.

Once a particular ligand has been chosen it must be bonded, or immobilized, to a first phase which will allow ready separation of the ligand/ligate complex from contaminating components. This first phase will generally be a solid phase, such as SEPHAROSE TM agarose gel particles or SEPHADEX TM cross-linked dextran particles beads adapted to facilitate chemical attachment of the ligand by a covalent bond. Other examples of solid phases include filter paper activated to specifically bond with a ligand, nitrocellulose, other microporous and molecular porous membranes, beads of agarose, dextran, latex, glass, polyacrylamide, collagen or similar gels, or cell organelles, or like biological substrates. The solid substrate may also be isolated from natural sources possessing naturally bound ligate. For example, the substrate may be a procaryotic or eucaryotic cell containing a specifically bound ligand such as an antibody, a hormone, or a cytokine. Bonding of a ligand can be by any conventional means, such as by cyanogen halide activation, sulfonyl chloride activation, or periodate activation of an insoluble polysaccharide, such as SEPHAROSE TM, SEPHADEX TM or cellulose, with a cyanate ester, sulfonate, or carboxyl functionality in order to chemically attach the ligand by a covalent bond to the solid substrate. Other suitable activating agents are well-known in the art. The ligand may also be adsorbed to the first phase.

A liquid phase may also be utilized. Here, the ligand is solubilized within a liquid phase that is generally immiscible with the liquid containing the ligate. This liquid phase has a greater affinity, or a higher partition coefficient, for the ligand and for the ligand/ligate complex, than the liquid containing the ligate. Contacting of the two immiscible liquids containing a ligand and ligate allows a ligand/ligate complex to form within the phase containing the ligand. Contaminating components within the ligate-containing solution are readily removed by separating the two liquid phases, e.g., by decantation.

The ligand may alternatively be bonded with a polymer which is soluble in a first set of environmental conditions, and insoluble in another set of environmental conditions. For example, a thermal phase separating polymer can be bonded with the ligand, the ligand introduced into the liquid containing the ligate, to allow ligand/ligate complex formation, and the polymer then caused to precipitate by raising the temperature of the liquid above the polymer's lower critical solution temperature. Monji et al., 14 Appl. Bioc. Biotech. 107, 1987. The precipitated polymer, which has the ligand/ligate complex bonded to it, is then washed to remove contaminating components.

If necessary, the ligand, rather than the first phase to which it is bonded, may be chemically modified to facilitate bonding of the ligand to the phase. Examples of suitable modifications are well known to those skilled in the art. In addition, the ligate may be chemically modified to cause it to be specifically recognized by the ligand. For example, if there is no appropriate or readily available ligand for the ligate desired to be purified, the ligate may be modified to introduce a molecule recognized by another ligand, and the interaction of that modification with the ligand used to purify the ligate. One example of a pair of molecules suitable for this modification include the specific binding pair avidin and biotin. Briefly, the desired ligate is formed with a biotin molecule covalently bonded to it, e.g., by standard biochemical or genetic engineering methodology. Avidin, the ligand, is provided bonded to a first phase as described above, and the biotin-ligate molecule purified by causing an avidin/biotin-ligate complex to form. The biotin-ligate molecule is then purified as described below, and used as a biotin-ligate molecule, or treated to remove the biotin moiety from the ligate, using standard procedures.

After the ligand has been bonded to a first phase it is then contacted with a second phase, normally an aqueous phase, containing the ligate, under conditions in which the ligand and ligate are contacted together to form a complex. This complex remains bonded to the first phase, with the ligand and ligate held together by one or more non-covalent pressure-sensitive bonds. The first phase is then washed, or otherwise treated, to remove the second phase and any non-specifically binding molecules, using standard techniques. For example, when the ligand is bonded to a solid phase, a solution containing the ligate is passed into intimate contact with the immobilized ligand so that the ligate specifically attaches to the immobilized ligand on the solid substrate, while the remainder of the solution and any contaminating material passes out of contact with the substrate. A buffer can then be passed over the solid substrate to more completely wash away contaminating material from the solid substrate, and from the ligand/ligate complex.

After formation of the ligand/ligate complex, and removal of contaminating compounds from the vicinity of the complex, the complex is pressurized to a pressure of at least 300 atmospheres under conditions sufficient to cause release of the ligate from the complex. This pressure is chosen to effect substantial dissociation of the ligand/ligate complex, and generally a pressure between 1,000 and 3,000 atmospheres is utilized, although pressures up to about 6,000 atmospheres may be used. It is advantageous to utilize a minimum pressure suitable for separating the complex with at least 80% efficiency, in order to minimize the chance of inactivation of the ligand or ligate by the pressure. Once the pressure is applied, the system is allowed to equilibrate for between about 5 minutes and 120 minutes, usually between 15 and 30 minutes, such that the ligate is maximally released from the complex.

If the desired ligate or ligand is sensitive to high pressure, losing a significant proportion of its biological activity, it may be necessary to modify the conditions under which the ligand/ligate complex is subjected to high pressure. This is generally only a problem for an oligomeric protein. Such an oligomeric protein can be stabilized under high pressure by causing a co-factor or co-enzyme of the protein to bond with the protein prior to subjecting it to high pressure. Alternatively, a multivalent ion, such as magnesium or phosphate, can be provided to stabilize the ligand or ligate without affecting its biological activity. Further, agents, such as glutaraldehyde, can be used to cross-link the oligomeric subunits of the protein without affecting the ability of the oligomer to form a ligand/ligate complex, and thereby stabilize the molecule at high pressure.

The buffer used during exertion of high pressure may also be chosen to prevent loss in biological activity. For example, an aqueous solution of ethylene glycol is a non-denaturing buffer which may lower the pressure required to dissociate the ligand/ligate complex.

It is also possible to use pressure conditions which cause only a temporary loss of biological activity of the oligomeric ligate or ligand. Biological activity of some oligomeric proteins is regained by simply allowing the monomers or multimers of the protein to reassociate, after reducing the pressure, to provide the biologically active molecule.

While pressure is maintained, or after the pressure has been released, the ligate released from the complex is separated from the immediate vicinity of the ligand by any of a number of standard procedures. For example, the first phase containing the ligand may be washed with a suitable buffer to remove the unbound ligate. Alternatively, the ligand-containing phase may be precipitated from the ligate-containing phase. For example, thermal phase separating polymers can be caused to precipitate from the solution, or a first phase of solid beads can be separated by use of gravity, or, if the beads are magnetic, by use of a magnet. In another method, the ligate may be subjected to an electric field to cause it to move from the vicinity of the ligand. For example, a voltage of between 1 and 100 V/cm, generally between 5 and 20 V/cm, can be provided for a period between 1 and 60 minutes, preferably between 5 and 10 minutes.

The decision whether to perform such separation before or after depressurization is dependent upon the speed at which the ligand and ligate are able to reform a complex. If possible, it is advantageous to separate the unbound ligate after depressurization, since a high pressure pump and receiving vessel are then not required. This is generally possible when the ligate is an oligomeric protein which is dissociated by high pressure, reassociates only slowly when the pressure is released, and only binds to the ligand in its reassociated state.

If dissociation of the ligand/ligate complex is not complete after the above process, increased recovery of ligate is obtained by utilizing a plurality of pressure cycles. Generally, between 1 and 10 cycles are suitable to obtain recovery greater than about 90% at a pressure of about 500 atmospheres.

After the ligate has been removed from the vicinity of the ligand, it may be recovered by any standard procedure.

EXAMPLE

This example illustrates the effect of elevated pressure in recovering an antigen from an immunoadsorbent. This example is not limiting to the invention, and those skilled in the art will recognize that any of the ligands, ligates and methods described above can be used in this invention.

In this example the ligand is a monoclonal antibody (mAb) to bovine serum albumin, and the ligate is bovine serum albumin (BSA). Electrophoresis is used to separate unbound ligate from ligand.

The ligand was bonded to a solid phase, an immunoadsorbent membrane, by covalently attaching anti-bovine serum albumin monoclonal antibody 9.1 (Morel et al., 25 Mol. Immunol. 7, 1988) to a regenerated cellulose microporous membrane (100 μm thickness, 0.45 μm pore size, Micro Filtration Systems, Dublin, Calif.) using tresyl chloride activation (Nilsson et al. 102 Bioc. Biop. Res. Comm. 449, 1981). The antibody was purified from mouse ascites by affinity chromatography using BSA-SEPAROSE agarose gel particles, as described by Olson et al., 3 Biotechnol. Prog. 177, 1987, and eluting with 0.1M glycine/HCl, pH 2.5. The BSA was Pentex sulfhydryl-modified BSA (Miles Labs, Naperville, Ill.) purified, and radiolabelled with $^{125}$I, as described by Olson et al., Id., to a specific activity of about 0.1 mCi/mg. A 23 cm$^2$ membrane sheet was reacted for 15 minutes with 60 μl tresyl chloride and 120 μl pyridine in 3 ml dried acetone, washed successively with solutions of acetone, 50:50 acetone: 1 mM HCl (v/v), and 1 mM HCl; and reacted with 1 mg antibody in phosphate buffer, pH 7.6.

The binding characteristics of the immobilized mAb were determined by radioimmunoassay as follows: 6.4 mm$^2$ membrane disks were combined with varying amounts of soluble $^{125}$I-BSA in a total volume of 160 μl and incubated overnight with orbital shaking. Membrane disks (blotted free of surface liquid) and 100 μl aliquots of solution were counted for gamma activity. The assay buffer was 0.15M Bis-Tris (Fisher Scientific, Fair Lawn, N.J.) with 0.02% sodium azide (BTA), and contained 0.1% (w/v) thyroglobulin to reduce non-specific adsorption. Control assays, performed using membranes containing equal loadings of irrelevant mouse immunoglobulin, showed that non-specific adsorption was not totally eliminated by the addition of thyroglobulin. Specific binding was determined by subtracting non-specific binding data from total binding data. These specific binding data were then fit to a Langmuir isotherm, where $q = QKc/(1+Kc)$, using nonlinear least-squares regression. Here, $q$ is the concentration of bound BSA (moles/liter total membrane volume), $Q$ is the saturation concentration of bound BSA, $K$ is the equilibrium association (or affinity) constant, and $c$ is the concentration of soluble BSA. The immunoadsorbent membrane possessed a moderate affinity for BSA of $2.4 \times 10^7 M^{-1}$, and a saturation capacity of 6.4 μmole/L membrane volume.

Membrane disks were cut from the above membrane, and a disk of 1.7 cm$^2$ size used in each assay. Each membrane was contacted for at least 2 hours with 0.5 ml of 0.15M bis-tris buffer at pH 7.0 containing 25 μg $^{125}$I-BSA to allow complex formation to occur. The contacting solution was then removed, and the membrane repeatedly rinsed in buffer.

A pressure vessel designed for 2000 atmospheres and equipped with two electrical feed-throughs was obtained from Fluitron (Ivyland, Pa.). The vessel was nominally 5 cm inner diameter and 300 cm$^3$ internal volume. The vessel interior was coated with Kinar to electrically insulate its contents. The pressure generator was a manual screw pump (High Pressure Equipment, Erie, Pa.). A flexible PVC cylinder filled with 0.15M Bis-Tris was suspended in the pressure vessel and fitted with an electrode to serve as anode. An electrode placed in a Bis-Tris solution exterior to the PVC cylinder served as cathode. The lower end of the cylinder was filled by a membrane "basket" (Spectrum Medical, Los Angeles, Calif.) which contained an immunomembrane with its associated ligand/ligate complex. The membrane basket was sealed on both ends with regenerated cellulose dialysis membranes impermeable to BSA, but permeable to buffer ions that complete the electric circuit.

Each membrane was placed into the buffer-filled chamber and pressurized for 15 minutes. For a first membrane pressurization was effected at 1 atmosphere, for a second membrane pressurization was effected at 1000 atmosphere. For a third and fourth membrane, pressurization was effected at 2000 atmosphere. After the 15 minute incubation at high pressure, the membrane was subjected to an electric field (100 mA current, about 10 V/cm) for 5 minutes to electrophorese dissociated BSA from the immunomembrane and into the liquid of the membrane basket. The apparatus was then depressurized, and the chamber fluid removed and analyzed for the presence of $^{125}$I-BSA. The apparatus was reassembled and the process repeated for a total of four pressurization-electrophoresis cycles. Following the fourth pressure cycle, the immunomembrane was contacted for one hour with a large excess of unlabelled BSA to cause dissociation of any remaining reversibly bound $^{125}$I-BSA.

After 4 pressurization-electrophoresis cycles at 2000 atmospheres about 90% of the reversibly bound antigen was recovered. After only one such cycle about 75% of the bound antigen was recovered. In contrast, only about 25% of the bound antigen was recovered after four cycles at 1 atmosphere. Intermediate recoveries were observed at 500 and 1000 atmospheres. Use of 30 minute, rather than 15 minute, periods of pressure did not increase recovery of bound antigen, indicating that a high pressure equilbrium state is reached within 15 minutes.

Repeated exposure to 2000 atmospheres had no discernable effect on the mAb affinity or capacity, the K and Q values remaining relatively constant.

Other embodiments are within the following claims.

We claim:

1. A method for purifying a biologically active ligate, comprising the steps of:
   (a) providing a ligand having a specific affinity for said ligate, said ligand being covalently bonded or adsorbed to a solid support,
   (b) providing said ligate within a phase,
   (c) contacting said solid support and said phase under conditions in which said ligand and ligate are contacted together to form a complex bonded to said solid support, said ligand and ligate being held together only by one or more non-covalent pressure-sensitive bonds,
   (d) separating at least a portion of said phase from said solid support by washing said solid support, to provide a purified solid support comprising said complex bonded to said solid support, (e) subjecting said purified solid support to a pressure of at least 300 atmospheres under conditions sufficient to cause release of said ligate from said complex, and not sufficient to cause significant release of said ligand from said solid support, said conditions not irreversibly causing the biological activity of said ligate to be significantly reduced, (f) separating said ligate released from said complex from the immediate vicinity of said ligand, and (g) recovering said ligate in its biologically active form.

2. The method of claim 1, wherein said subjecting step comprises subjecting said purified solid support to a pressure under conditions insufficient to cause significant reduction in the biological activity of said ligand.

3. The method of claim 1 or 2, wherein said phase is a liquid.

4. The method of claim 1, wherein said subjecting step comprises applying a pressure of at least 500 atmospheres.

5. The method of claim 4, wherein said subjecting step comprises applying a pressure between 500 and 3000 atmospheres.

6. The method of claim 4, wherein said subjecting step comprises applying a pressure between 1000 and 3000 atmospheres.

7. The method of claim 4, wherein said subjecting step comprises applying a pressure of less than 6000 atmospheres.

8. The method of claim 1, wherein said steps of subjecting to a pressure and separating said released ligate are repeated at least once.

9. The method of claim 1, further comprising separating substantially all said phase from said solid support prior to said subjecting step.

10. The method of claim 1, wherein said step of separating said ligate released from said complex is performed while said pressure is maintained.

11. The method of claim 1, wherein said step of separating said ligate released from said complex comprises washing said ligate from said ligand with a solvent.

12. The method of claim 1, wherein said step of separating said ligate released from said complex comprises subjecting said ligate to an electric field to remove said ligate from the vicinity of said ligand.

* * * * *